United States Patent [19]

Tanino et al.

[11] Patent Number: 4,571,310

[45] Date of Patent: Feb. 18, 1986

[54] PROCESS FOR PREPARING ALKOXYPHOSPHONITRILE COMPOUNDS

[75] Inventors: Hiroshi Tanino, Hasuda; Tetsuhiko Okamoto, Tokyo; Shinichiro Ueyama, Tokyo; Kazuhiko Fuzikawa, Tokyo, all of Japan

[73] Assignee: Shin Nisso Kako Co., Ltd., Japan

[21] Appl. No.: 613,284

[22] Filed: May 23, 1984

[30] Foreign Application Priority Data

May 26, 1983 [JP] Japan ................................. 58-91453

[51] Int. Cl.4 ............................................. C07F 9/24
[52] U.S. Cl. ................................ 260/973; 260/927 N
[58] Field of Search .......................... 260/973, 927 N

[56] References Cited

U.S. PATENT DOCUMENTS 4,451,410  5/1984  Shibata ................................. 260/973

OTHER PUBLICATIONS

Unverified Translations of the claims of Japanese 109320/1974, 35300/1975, 41889/1983, and 130170/1983.

Fedorov et al., "Current Abstracts of Chemistry", vol. 94, Issue 1080, (1984).

*Primary Examiner*—Anton H. Sutto
*Attorney, Agent, or Firm*—Abelman Frayne Rezac & Schwab

[57] ABSTRACT

A process for preparing alkoxyphosphonitrile compounds.

3 Claims, No Drawings

PROCESS FOR PREPARING ALKOXYPHOSPHONITRILE COMPOUNDS

This invention relates to a novel process for preparing alkoxyphosphonitrile compounds, more particularly to a process for preparing a mixture of alkoxyphosphonitrile oligomer with poly(alkoxyphosphonitrile oligomer) having desired physical properties with high reproducibility.

As to the alkoxyphosphonitrile oligomers, which are obtainable by alkoxylation of the phosphonitrile chloride oligomer having a cyclic or linear constitution (I):

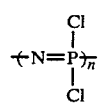

(wherein n is an integer of not less than 3), particularly cyclic phosphonitrile chloride oligomers (II) and (III) (the case in which n is 3 or 4):

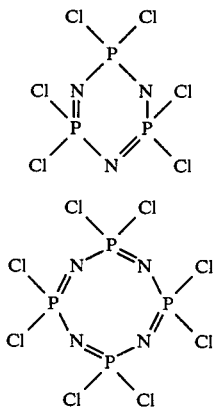

or a mixture of phosphonitrile chloride oligomers containing them as major components, or poly(alkoxyphosphonitrile oligomer) prepared by condensation of the said alkoxyphosphonitrile oligomers, there have been developed many uses as various kinds of industrial materials because of their excellent heat-resistance, low-temperature resistance, lubricating property, electric insulating property or chemical stability. And especially the mixtures of alkoxyphosphonitrile oligomers and poly(alkoxyphosphonitrile oligomers) are being watched with keen interest as flame retardants.

In Japanese Patent Laid-Open-to-Public Publication Nos. 109320/1974 and 35300/1975, there are described processes for preparing the mixture of alkoxyphosphonitrile oligomer with poly(alkoxyphosphonitrile oligomer) by reacting phosphonitrile chlorides oligomer with metal alkoxide, or reacting with alcohol in the presence of tertiary amine such as pyridine or triethyl amine as acid acceptor to prepare alkoxyphosphonitrile oligomer having still remaining chlorine atoms combined with the nucleus thereof, followed by partial condensation reaction with the alkoxyphosphonitrile oligomers. According to such processes it is possible to obtain flame retardants showing excellent performances in application to rayon, for example. However, the processes as disclosed therein have difficulties in controlling excessive condensation, and this makes it difficult to set the reaction condition for obtaining the product having desired viscosity or molecular weight distribution and therefore it is not easy to insure reproducibility of the properties of the product.

In Japanese Patent L-O-P Publication No. 41889/1983, there is disclosed a process for preparing a mixture of alkoxyphosphonitrile oligomer with poly(alkoxyphosphonitrile oligomer) by using cheap alkali metal carbonate salts as acid acceptor in substitution for the high-cost metal alkoxides or tertiary amines. Namely there is described a process in which phosphonitrile chloride oligomer is reacted with alcohol in the presence of alkali metal carbonate (the first step), then the water produced by reaction is removed by distillation (the second step), and thereafter reacting with metal alkoxide (the third step) to obtain the mixture of alkoxyphosphonitrile oligomer with poly(alkoxyphosphonitrile oligomer). However, in this process, the water produced in the first step gives side reactions such as reaction with the active chlorine atoms which are still remaining in the phosphonitrile oligomer combining with the nucleus of the oligomer during the reaction of the first step and the second step, or hydrolyzation of the alkoxy groups attached already to the phosphonitrile nucleus. As the result, the coexistence of phosphonitrile oligomer and poly(phosphonitrile oligomer) having OH groups attached to phosphonitrile nucleus in the reaction product is not avoidable. Thus, because of the largeness of solubility to water of such substances having OH groups therein, in producing the product containing such substances, for example, in producing flame-resistant rayon by adding such substance to viscose solution, a part of phosphonitrile oligomers or poly(phosphonitrile oligomers) are eluted in spinning bath and the produced rayon cannot have predetermined flame-resistant property. Furthermore, the rayon containing such substance shows a remarkable decrease of flame-resistant property by repeated washing.

This invention comprises (1) a partial alkoxylation reaction in which phosphonitrile chloride oligomer is alkoxylated partially leaving a part of chlorine atoms contained therein (the first step reaction), (2) a reaction in which dealkyl-chlorization reaction between the active chlorine atoms still remaining in phosphonitrile oligomer combining with their nucleus (hereinafter referred to as "remaining active chlorine atoms") and alkoxy group already combined with phosphonitrile oligomer is taken place to cause condensation between phosphonitrile oligomers, for example, such as

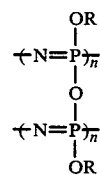

to a predetermined degree (the second step reaction), and a reaction in which the remaining active chlorine atoms still present at the time of termination of the second step reaction are substituted perfectly with alkoxy groups (the third step reaction).

Namely, this invention is a process for preparing phosphonitrile compound having alkoxy groups, which process comprises;

(A) the first step in which phosphonitrile chloride oligomer is reacted with alcohol of an amount of from 0.2 to 0.8 equivalent per 1 equivalent of active chlorine atoms contained in said phosphonitrile chloride oligomer, in the presence of organic tertiary amine of an amount of not less than the equivalent to said alcohol at a temperature below 20° C., to substitute about 34 to 75 percent of said active chlorine atoms with alkoxy groups, (B) the second step in which the temperature is then elevated to cause condensation through liberation of alkyl chlorides, and (C) the third step in which a reaction is performed by adding alcohol to reaction mixture at an amount of not less than the equivalent to the active chlorine atoms still remaining at the time of termination of the second step to substitute the remaining active chlorine atoms with alkoxy groups substantially perfectly.

The "active chlorine atoms" as used herein is to designate the chlorine atoms which are combined with the phosphorus atoms in phosphonitrile oligomer as shown by the formulae (I), (II) or (III).

Essential points of the feature of this invention are as follows:

(1) By selecting the amount of alcohol to be used in the first step within the range of from 0.2 to 0.8 equivalent per 1 equivalent of active chlorine atoms and preventing the liberation of alkyl chlorides by controlling the reaction temperature of the first step below 20° C., it becomes possible to set optionally the amount of active chlorine atoms at the time of termination of the first step. And in the first step, only substitution of active chlorine atoms by alkoxy groups takes place to check the occurrence of condensation reaction. This is extremely convenient to advance the total reaction of this invention stepwise while controlling it.

(2) Condensation through liberation of alkyl chlorides is performed at low temperature as compared to the prior art processes and this facilitates the control of condensation degree. Abundance of the amount of remaining active chlorine atoms at the time of termination of the first step makes it possible to perform the liberation of alkyl chlorides at low temperature. Incidentally, the amount of remaining active chlorine atoms in the phosphonitrile compound prepared by substituting 34 to 75 percent of active chlorine atoms contained in phosphonitrile chloride oligomer with alkoxy groups is 16 to 40 percent by weight, when alkoxy group is propoxy group.

(3) In the third step, condensation does not take place substantially and only alkoxylation advances almost quantitatively. Thus the remaining active chlorine atoms do not exist substantially in the final product (less than about 0.5% by weight).

As set forth hereinabove, by the process of this invention it becomes possible to prepare alkoxyphosphonitrile compounds having desired condensation degree and molecular weight distribution and substantially having no remaining active chlorine atoms in high reproducibility.

As the phosphonitrile chloride oligomer to be used as starting raw material in this invention, a mixture of various substances represented by the general formula (I) obtained in accordance with the common process by the reaction of phosphorus pentachloride with ammonium chloride is usable or it may be possible to use the phosphonitrile chloride oligomer represented by the formula (II) or (III) isolated from such mixture by proper means (for example by the process as described in Japanese Patent L-O-P Publication No. 130107/1983) in single or in combination, depending upon the utility purposes of the finally finished product.

Alcohols to be used in this invention include, for example, saturated aliphatic alcohols such as methanol, ethanol, propanol, butanol, pentanol, octanol (including several kinds of isomers) or trifluoroethanol; unsaturated aliphatic alcohols such as allyl alcohol; phenols such as phenol, cresol and bromophenol; aralkyl alcohols such as benzyl alcohol; and alicyclic alcohols such as cyclohexanol; however, they are not limited only thereto. Those alcohols may not necessarily be the same between the ones to be used in the first step and the ones to be used in the third step, and according to circumstances it is possible to use more than two of them as a mixture in each of the first step and the third step.

The organic tertiary amines to be used in this invention include, for example, trimethyl amine, triethyl amine, tripropyl amine, tributyl amine, trioctyl amine, N-methyl-N-ethylpropyl amine, N,N-diethyl propyl amine, N,N-dimethyl cyclohexyl amine, N,N-dimethyl aniline, N,N-diethyl aniline, N,N-diethyltolyl amine, N,N-dimethylbenzyl amine, triethylene diamine, quinuclidine, N-methyl pyrrolidine, N-methyl piperidine, N,N'-dimethyl piperadine, pyridine, $\alpha$-,$\beta$- and $\gamma$-picoline, 5-ethyl-2-picoline and trimethyl pyridine, however they are not limited thereto. And those tertiary amines are usable in combination.

The metal alkoxides to be used in the third step are prepared, for example, by reacting the above-mentioned alcohol with a metal such as potassium, sodium, calcium, magnesium and aluminum, however it is common to use potassium or sodium. Further, when the alcohol is phenol or its homolog, the metal compound is also obtainable by reacting phenol or its homolog with a metal hydroxide (e.g. potassium hydroxide or sodium hydroxide) and then removing generated water.

In this invention it is advantageous to perform the reaction in inactive organic solvent, and such solvents include, for example, benzene, toluene, xylene, monochlorobenzene, tetrahydrofuran and dioxane, however, they are not limited only thereto.

The reaction of this invention is carried out, for example, in the following manner.

In the first step, in a suitable solvent, alcohol and organic tertiary amine of given amounts are mixed to give a solution, to which 20 to 40 percent solution of phosphonitrile chloride oligomer dissolved in proper solvent is added dropwise with stirring at a temperature below 20° C., preferably below 10° C., and more preferably at a temperature about 0° C. or further below. In this case the temperature above 20° C. is not favorable because condensation reaction by liberation of alkyl chloride may take place simultaneously. The time requested for the dropping of solution is not limited specifically but the time of from 1 to 2 hours is suitable. The amount of alcohol to be used in this step is chosen within the range of from 0.2 to 0.8 equivalent per 1 equivalent of active chlorine atoms contained in phosphonitrile chloride oligomer, depending on the condensation degree or molecular weight distribution requested for the final product. The alcohol added is spent only for alkoxylation reaction correctly. And the amount of tertiary amine is more than 1 equivalent per 1 equivalent of alcohol used and its excessive use is effective to hasten the reaction.

The second step is carried out in succession to the termination of the first step by elevating reaction temperature. In this step it is sufficient to set the reaction temperature and reaction time adequately depending on desired condensation degree or molecular weight distribution, since the object of this step is to perform condensation with splitting off alkyl chloride. It is preferable to perform the reaction for the time of from 1 to 10 hours at a temperature of 20° to 60° C., more preferably for 6 to 8 hours, at 30° to 35° C. Reaction product is subjected to gel permeation chromatography (GPC) during reaction, and the reaction is finished at the time when desired molecular weight distribution is observed.

The third step is to react the remaining active chlorine atoms at the time of termination of the second step. As this process, there are two processes such as "Process A" in which alcohol is reacted with organic tertiary amine using this amine as acid acceptor, and "Process B" in which the alcohol is reacted in the form of metal alkoxide. It is necessary to use alcohol and organic tertiary amine in Process A and metal alkoxide in Process B at an amount of more than 1 equivalent per 1 equivalent of remaining active chlorine atoms determined at the time of termination of the second step, and it is preferable to use more than 1.5 equivalent. In Process A, when organic tertiary amine added at the first step is remaining in sufficient amount in the form of free base, there is no need to add it in the third step additionally. In order to check the condensation reaction which can take place as side reaction, it is ideal to complete the alkoxylation by carring out the reaction at a temperature within the range of 20° to 50° C. for a long time (e.g. 40 hours). For instance, however, when the reaction is continued for 6 to 10 hours at 20° to 50° C., then temperature is elevated to about 80° C. to complete alkoxylation, condensation reaction does not take place substantially.

After completion of the third step, excessive alcohol, organic tertiary amine and organic solvent are recovered by distillation under reduced pressure (when metal alkoxide is used as alkoxylating agent, it is evident that the metal alkoxide should have been decomposed with water beforehand.); the residue of distillation is dissolved by adding water-immiscible inactive solvent; and the solution is washed with dilute acid, dilute alkali and pure water, dried with drying agent, then the solvent is distilled off completely under reduced pressure. Thus alkoxyphosphonitrile compound, the object of this invention, is obtained generally as slightly yellow, viscous liquid. The alkoxyphosphonitrile compound thus obtained has excellent performance as flame retardant for rayon. The recovered tertiary amine, alcohol and organic solvent are, of course, usable again as they are or after purifying by proper methods.

EXAMPLE 1

116.0 g of mixture of phosphonitrile chloride oligomers (containing 54.6% of cyclic triphosphonitrile chloride, 15.1% of cyclic tetraphosphonitrile chloride and 30.3% of other phosphonitrile chloride oligomers) synthesized according to usual process by the reaction of phosphorus pentachloride with ammonium chloride is dissolved in 302.8 g of monochlorobenzene to prepare 27.7% solution. 60.0 g of n-propyl alcohol (0.5 equivalent to active chlorine atoms) and 237.0 g of pyridine (3.0 equivalents to n-propyl alcohol) were charged into 1 liter four-necked flask having stirrer, reflux condenser, thermometer and dropping funnel, and the mixture was cooled to −5° C. in salt-ice bath with stirring. The monochlorobenzene solution of the mixture of phosphonitrile chloride oligomers was dropped taking 90 minutes. Temperature of the reaction liquid was 10° C. when dropping was finished. Reaction was continued further for 30 minutes at said temperature after termination of dropping (the above is the first step), then warmed gradually with warm waterbath and condensation reaction was carried out for 9 hours at temperatures of 35±2° C. Remaining active chlorine atoms of this condensation reaction product were determined as 19.7% (the above is the second step).

120.0 g of n-propyl alcohol (2.5 equivalent to remaining active chlorine atoms) was added dropwise to aforementioned reaction liquid taking about 1 hour keeping the temperature at 35±2° C., stirring was continued for 6 hours after initiation of dropping at said temperature, then temperature was elevated and reaction was continued for more 6 hours at 80±2° C. The amount of remaining active chlorine atoms was 0.50% at this time. The reaction was stopped and 350 g of mixed solution of excess n-propyl alcohol and pyridine with monochlorobenzene was distilled off at internal temperature of 60° to 70° C. under reduced pressure. 100 ml of monochlorobenzene and 50 ml of water were added to the residue, pH of water layer was adjusted to 1.0 with hydrochloric acid, then water layer was separated. The organic layer was washed with 100 ml of 5% solution of sodium bicarbonate then with 100 ml of water, then dehydrated by adding 50 g of anhydrous sodium sulfate and then filtered. Monochlorobenzene was distilled off completely from this filtrate under reduced pressure of 1 mmHg to give 122.3 g of slightly yellow, viscous liquid. It was 75% in yield, 3.750 cps in viscosity at 25° C. and 0.50% in remaining active chlorine atoms. The reaction product was determined as alkoxyphosphonitrile oligomer containing poly(alkoxyphosphonitrile oligomer) based upon the absorption of —P—O—P— bond appeared in the vicinity of 1.000–870 cm$^{-1}$ by IR analysis.

EXAMPLE 2

An experiment was conducted in the same manner as in Example 1 except that in the first step the amount of n-propyl alcohol charged preliminarily into 1 liter four-necked flask was changed to 84.0 g (1.4 mol) and the amount of n-propyl alcohol to be dropped in the third step reaction to 96 g (1.6 mol) to give 124.2 g (76.2% yield) of slightly yellow, viscous liquid. Physical properties of the obtained product were tabulated in Table 1.

EXAMPLE 3

An experiment was conducted in the same manner as in Example 1 except that in the first step the amount of n-propyl alcohol charged preliminarily into 1 liter four-necked flask was changed to 36.0 g (0.6 mol) and the amount of n-propyl alcohol to be dropped in the third step reaction to 144.0 g (2.4 mol) to give 107.3 g (65.8% yield) of slightly yellow, viscous liquid. Physical properties of the obtained product were shown in Table 1.

EXAMPLE 4

An experiment was conducted in the same manner as in Example 3 except that the duration of condensation reaction was changed to 3.5 hours to give 112.3 g (68.9% yield) of slightly yellow, viscous liquid. Physical properties of the obtained product were shown in Table 1.

EXAMPLE 5

An experiment was conducted in the same manner as in Example 3 except that the duration of condensation reaction was changed to 2.0 hours to give 120.6 g (74.0% yield) of slightly yellow, viscous liquid. Physical properties of the obtained product were exhibited in Table 1.

EXAMPLE 6

An experiment was conducted in the same manner as in Example 1 except that the amount of n-propyl alcohol charged preliminarily into 1 liter four-necked flask was changed to 24.0 g (0.4 mol), the duration of condensation reaction to 2.5 hours, and the amount of n-propyl alcohol to be dropped in the third step reaction to 156.0 g (2.6 mol) to give 124.0 g (76.1% yield) of slightly yellow, viscous liquid. Physical properties of the obtained product were given in Table 1.

TABLE 1

| Examples | Viscosities (cps) at 25° C. | Amounts of remaining active chlorine atoms (%) |
|---|---|---|
| 2 | 1,200 | 0.46 |
| 3 | 100,000 | 0.50 |
| 4 | 7,960 | 0.49 |
| 5 | 1,680 | 0.48 |
| 6 | 1,095 | 0.43 |

EXAMPLE 7

18.0 g (0.3 mol) of n-propyl alcohol and 1.1 g (0.9 mol) of pyridine were charged into a 500 ml four-necked flask having the same devices as used in Example 1, and the mixture was cooled to −5° C. with salt-ice bath with stirring. 150 ml of monochlorobenzene solution containing 34.8 g (0.1 mol) of cyclic triphosphonitrile chloride (the equivalent of said n-propyl alcohol to the active chlorine atoms therein was 0.5) was added dropwise through a dropping funnel at temperature of from −5° to 0° C., and reaction was continued at same temperature for 2 hours from the initiation of dropping. Temperature was elevated gradually with warm water-bath and condensation reaction was carried out for 6 hours at 35±2° C. The rate of remaining active chlorine atoms at the time of termination of condensation reaction was found to be 18.7%. Further into this reaction liquid 36.0 g (0.6 mol) of n-propyl alcohol (2.7 times the equivalent to the remaining active chlorine atoms) was added at once and alkoxylation reaction was carried out for 2 hours at 35±2° C., then the temperature was elevated and the reaction was continued for 6 hours at 80±2° C. to complete. After-treatment was applied in the same manner as in Example 1 to give 26.2 g of slightly yellow, viscous liquid which was 10,000 cps in viscosity at 25° C. and 0.49% in remaining active chlorine atoms.

EXAMPLE 8

An experiment was conducted in the same manner as in Example 7 except that the amount of n-propyl alcohol charged preliminarily into 500 ml four-necked flask is changed to 10.8 g (0.18 mol) and the amount of n-propyl alcohol to be added in the third step reaction to 43.2 g 0.72 mol) to give 18.7 g of slightly yellow, viscous liquid whose physical properties were shown in Table 2.

EXAMPLE 9

An experiment was conducted in the same manner as in Example 7 except that the amount of n-propyl alcohol charged preliminarily into 500 ml four-necked flask was changed to 25.2 g (0.42 mol) and the amount of n-propyl alcohol to be dropped in the third step reaction to 28.8 g (0.48 mol) to yield 29.5 g of slightly yellow, viscous liquid, whose physical properties were listed in Table 2.

EXAMPLE 10

An experiment was conducted in the same manner as in Example 7 except that the raw material was changed to cyclic tetraphosphonitrile chloride to give 46.6 g of slightly yellow, viscous liquid, and physical properties thereof were listed in Table 2.

EXAMPLE 11

An experiment was conducted in the same manner as in Example 8 except that the raw material was changed to cyclic tetraphosphonitrile chloride to give 45.6 g of slightly yellow, viscous liquid, and the physical properties thereof was shown in Table 2.

EXAMPLE 12

An experiment was conducted in the same manner as in Example 9 except that the raw material was changed to cyclic tetraphosphonitrile chloride to give 46.8 g of slightly yellow, viscous liquid, and the physical properties thereof was shown in Table 2.

TABLE 2

| Examples | Viscosities (cps) at 25° C. | Amounts of remaining active chlorine atoms (%) |
|---|---|---|
| 8 | 120,000 | 0.15 |
| 9 | 350 | 0.50 |
| 10 | 61 | 0.17 |
| 11 | 680 | 0.02 |
| 12 | 58 | 0.16 |

EXAMPLE 13

60.0 g (1.0 mol) of n-propyl alcohol and 303.6 g (3.0 mol) of triethylamine were charged into the same 1 liter four-necked flask as used in Example 1 and the mixture was cooled with salt-ice bath to −5° C. with stirring, and to which 418.8 g of 27.7% monochlorobenzene solution of phosphonitrile chloride oligomers mixture as used in Example 1 was added dropwise through a dropping funnel. The temperature of reaction liquid was maintained below 10° C. The reaction was performed for 2 hours while maintaining the temperature at the same level from the initiation of dropping. The reaction mixture was heated gradually with warm water-bath and then subjected to condensation reaction for 9 hours at temperatures of 35±2° C. After termination of condensation reaction, excess triethylamine was distilled off under reduced pressure and 50 ml of water was added to the residue. The water layer was separated after adjusting its pH to 1.0 with hydrochloric acid, and the organic layer was washed with 100 ml of 5% water-solution of sodium bicarbonate and further washed with 100 ml of water, then dehydrated with 50 g anhydrous sodium sulfate. After such treatment, the amount of the remaining active chlorine atoms in the reaction liquid (the dehydrated organic layer) was found to be 20.1%. To this reaction liquid 94.8 g (1.2 mol) of pyridine was added, then 87.2 g (1.5 mol) of allyl alcohol, that is the amount of 2.0 times mol with respect to the remaining active chlorine atoms, was added dropwise taking about 1 hour while maintaining the temperature at 35±2° C., and reaction was carried out for 1.5 hours at the same temperature from the initiation of dropping. Reaction temperature was elevated further and reaction was continued for 8 hours at temperatures 60±2° C. After the reaction, excess allyl alcohol, pyridine and monochlorobenzene were distilled off under reduced pressure at internal temperature of 50°-60° C. to give a residue, to which 100 ml of monochlorobenzene and 50 ml of water were added, and after adjusting the pH of water layer with hydrochloric acid to 1.0 the water layer was separated. The organic layer thus obtained was washed with 100 ml of 5% water-solution of sodium bicarbonate, then with 100 ml of water, and then dehydrated with 50 g of anhydrous sodium sulfate and filtration followed. From this filtrate monochlorobenzene was distilled off completely under reduced pressure of 1 mmHg to give 115.2 g of slightly yellow, viscous liquid. The product was confirmed to have carbon-carbon double bond and —P—O—P— bond by IR analysis. And it was also found by NMR analysis that the ratio of propoxy group/allyloxy group in the product was 1:1. Further, it had viscosity of 2,120 cps at 25° C. and 0.2% of remaining active chlorine atoms.

EXAMPLE 14

In this experiment the reactions of the first step and the second step were conducted in the same manner as in Example 1. After termination of the second step reaction, 100 ml of water was added to the reaction liquid, pH of the water layer was adjusted to 1.0 with hydrochloric acid, and the water layer was separated. Organic layer thus obtained was washed with 100 ml of 5% water-solution of sodium bicarbonate then with 100 ml of water, then dried with 50 g of anhydrous sodium sulfate, and then followed filtration. From the filtrate pyridine and monochlorobenzene were removed by distillation under reduced pressure to give a slightly yellow, viscous liquid as the product of the second step reaction. By analysis, this product was confirmed to contain 19.4% of remaining active chlorine atoms. To this intermediate product 410.0 g of 20% n-propanol solution of sodium n-propoxide was added and reaction was performed under reflux for 2 hours (at about 95° C.) n-Propanol was then distilled off under reduced pressure at temperatures of from 50° to 70° C. 200 ml of monochlorobenzene and 300 ml of water were then charged into reactor and heated to 50° C. to dissolve the residue, then allowed to stand to remove the separated water layer. To the organic layer 200 ml of water was added, and after sufficient stirring pH of the water layer was adjusted to 7 with hydrochloric acid. The organic layer was washed with 100 ml of 5% water-solution of sodium bicarbonate, then with 200 ml of water, further dehydrated with 50 g of anhydrous sodium sulfate and filtered. From this filtrate monochlorobenzene was removed by distillation under reduced pressure to give 127.5 g (78.2% yield) of slightly yellow, viscous liquid. This product was 2,890 cps at 25° C. in viscosity and 0.35% in remaining active chlorine atoms.

What is claimed is:

1. A process for preparing alkoxyphosphonitrile compounds using phosphonitrile chloride oligomer and alcohol as raw materials, which comprises
   (a) a first step wherein phosphonitrile chloride oligomer is reacted with alcohol of an amount of 0.2 to 0.8 equivalent per 1 equivalent of active chlorine atoms contained in said phosphonitrile chloride oligomer, in the presence of organic tertiary amine of an amount of not less than the equivalent to said alcohol at a temperature below 20° C., to substitute about 34 to 75 percent of said active chlorine atoms with alkoxy groups,
   (b) a second step wherein temperature is elevated to cause condensation through liberation of alkyl chloride, and
   (c) a third step wherein alcohol of an amount of not less than the equivalent to the active chlorine atoms remaining at the time of termination of the second step is added to reaction system to cause reaction thereby to substitute said remaining active chlorine atoms with alkoxy groups substantially perfectly, the reaction being carried out in the presence of an inactive organic solvent.

2. The process for preparing alkoxy phosphonitrile compounds according to claim 1 wherein the third step comprises adding alcohol of an amount of not less than 1 equivalent and an organic tertiary amine of an amount of not less than 1 equivalent per 1 equivalent of the remaining active chlorine atoms to reaction system thereby to cause reaction.

3. The process for preparing alkoxyphosphonitrile compounds according to claim 1 wherein the third step is characterized by using the alcohol in the form of metal alkoxide.

* * * * *